US011363977B2

(12) United States Patent
Renlund et al.

(10) Patent No.: US 11,363,977 B2
(45) Date of Patent: Jun. 21, 2022

(54) SUCTION APPLYING DEVICE, AN APPARATUS FOR SAMPLING A BODILY FLUID AND A METHOD FOR DETECTING A COMPONENT IN A BODILY FLUID

(71) Applicant: Ascilion AB, Kista (SE)

(72) Inventors: Markus Renlund, Åkersberga (SE); Pelle Rangsten, Storvreta (SE); Mikael Hillmering, Solna (SE); Mikael Franzén, Drottningholm (SE)

(73) Assignee: Ascilion AB, Kista (SE)

( * ) Notice: Subject to any disclaimer, the term of this patent is extended or adjusted under 35 U.S.C. 154(b) by 142 days.

(21) Appl. No.: 16/628,561

(22) PCT Filed: Jul. 3, 2018

(86) PCT No.: PCT/EP2018/067941
§ 371 (c)(1),
(2) Date: Jan. 3, 2020

(87) PCT Pub. No.: WO2019/020327
PCT Pub. Date: Jan. 31, 2019

(65) Prior Publication Data
US 2020/0205708 A1    Jul. 2, 2020

(30) Foreign Application Priority Data

Jul. 25, 2017 (EP) .................................... 17183035

(51) Int. Cl.
*A61B 5/157* (2006.01)
*A61B 5/15* (2006.01)

(52) U.S. Cl.
CPC ........ *A61B 5/157* (2013.01); *A61B 5/150022* (2013.01); *A61B 5/150099* (2013.01); *A61B 5/150389* (2013.01); *A61B 5/150984* (2013.01)

(58) Field of Classification Search
CPC ........ A61B 5/150099; A61B 5/150145; A61B 5/150022; A61B 5/150213;
(Continued)

(56) References Cited

U.S. PATENT DOCUMENTS

| 4,813,433 A | * | 3/1989 | Downey | ............ | A61B 5/15003 |
| | | | | | 600/578 |
| 6,603,987 B2 | * | 8/2003 | Whitson | ............ | A61B 5/14514 |
| | | | | | 422/550 |

(Continued)

FOREIGN PATENT DOCUMENTS

| JP | S62-167569 A | 7/1987 |
| JP | S62-164006 U | 10/1987 |

(Continued)

OTHER PUBLICATIONS

A. Turner, "Biosensors: sense and sensibility," *Chem Soc. Review*, The Royal Society of Chemistry, vol. 42, No. 8, Apr. 21, 2013, pp. 3184-3196.

*Primary Examiner* — Patrick Fernandes
*Assistant Examiner* — Severo Antonio P Lopez
(74) *Attorney, Agent, or Firm* — Blank Rome LLP (57) ABSTRACT

A suction applying device (10) for applying suction to a sampling unit (50) for sampling bodily fluid, wherein the suction applying device comprises a syringe body (12) with a hollow interior (14) and a piston (20) movable inside the hollow interior of the syringe body. The syringe body has a rear end (16) through which a piston rod (21) connected to the piston extends outside of the syringe body and by means of which the piston can be moved, and a front end (18) opposite the rear end. The suction applying device further comprises a connection arrangement (130) configured for connection of a sampling unit, wherein the connection arrangement is located at the front end of the syringe body. The suction applying device also comprises a first conduit (40) having a rear opening (41) connecting the first conduit to a rear portion (14b) of the hollow interior, in which rear portion a sub-pressure is created when the piston is moved forward inside the hollow interior, and a front opening (42) by means of which the first conduit is connectable to a (Continued)

sampling unit. The suction applying device also comprises a second conduit (46) that connects a front portion (14*a*) of the hollow interior with the exterior of the syringe body, and which front portion is located between the piston and the front end of the syringe body. Also disclosed is an apparatus for sampling bodily fluid, comprising a suction applying device and a sampling unit, as well as a method for detecting a component in a bodily fluid.

15 Claims, 5 Drawing Sheets

(58) Field of Classification Search
CPC ........ A61B 5/150389; A61B 5/150984; A61B 5/15105; A61B 5/157; A61B 2217/005; A61B 18/1492; A61B 2017/306; A61B 2017/22079; A61B 10/0283; A61B 2018/00291; A61B 2218/007; A61B 10/0045; A61B 2017/00561; A61B 5/153
See application file for complete search history.

(56) References Cited

U.S. PATENT DOCUMENTS

| | | | |
|---|---|---|---|
| 7,927,290 B2 | 4/2011 | Fujiwara et al. | |
| 9,833,474 B2* | 12/2017 | Woodell-May | C12N 5/0645 |
| 2004/0002121 A1* | 1/2004 | Regan | A61B 5/150305 |
| | | | 435/7.2 |
| 2004/0106903 A1* | 6/2004 | Shue | A61B 5/150732 |
| | | | 604/168.01 |
| 2009/0177117 A1* | 7/2009 | Amano | A61B 5/1513 |
| | | | 600/583 |

FOREIGN PATENT DOCUMENTS

| | | | | |
|---|---|---|---|---|
| JP | 2004-503342 A | 2/2004 | | |
| WO | WO 01/43643 A1 | 6/2001 | | |
| WO | WO 02/05890 | 1/2002 | | |
| WO | WO 03/039369 A1 | 5/2003 | | |
| WO | WO 2007/077930 | 7/2007 | | |
| WO | WO 2015/187066 A1 | 12/2015 | | |
| WO | WO-2015187066 A1 * | 12/2015 | ............. | A61B 5/157 |
| WO | WO 2017/095321 A1 | 6/2017 | | |

\* cited by examiner

SUCTION APPLYING DEVICE, AN APPARATUS FOR SAMPLING A BODILY FLUID AND A METHOD FOR DETECTING A COMPONENT IN A BODILY FLUID

TECHNICAL FIELD OF THE INVENTION

The present invention relates to a suction applying device for applying suction to a sampling unit for sampling bodily fluid. The present disclosure also relates to an apparatus for sampling a bodily fluid, which apparatus comprises a suction applying device and a sampling unit comprising a microneedle device. The disclosure also relates to a method for detecting a component in a bodily fluid.

BACKGROUND

In clinical diagnostics, the analysis of bodily fluids, particularly of blood, is an important method used to study the health of a patient. The most frequent analyses are carried out in the home-care sector by the patient himself using capillary blood. For these applications, particularly for the determination of blood glucose levels, patients use lancing aids in order to slightly injure the skin and obtain a small drop of blood. This blood sample is typically applied to a test strip that is evaluated in a measuring apparatus. So as to simplify this complex procedure and minimize the patient's pain, numerous methods and technologies have been developed. It has for example been attempted to reduce the volume of blood required for analysis. This can be achieved, for example, in that the diameter of the lancing needle is reduced and the lancing depth is precisely adjustable. A thin lancing needle on the other hand produces only a small injury of the skin, so that only a little or no blood at all is obtained. Additional auxiliary measures have also been proposed, such as pressing the skin together or periodically stimulating the skin at the piercing site, e.g. with vibration, as well as using the suction effect of a vacuum that is produced to allow the amount of blood that is obtained to be increased.

It is also previously known to use so called microneedles when taking blood samples for e.g. performing a glucose test. The microneedle would have a capillary bore for withdrawing the blood. Usually a number of microneedles are provided on a substrate, and a sub-pressure, relative the atmospheric pressure, is provided to the bore of the microneedle.

With hollow microneedles a new type of pain-free general extraction method of bodily fluids can be used in conjunction with any biosensor. The skin penetration with microneedles is perceived as minimally invasive and causes no pain, with needles too short to reach sensory nerves in the skin. It can utilize interstitial fluid (ISF), instead of blood, as measurement media, extracted through a matrix of sub-millimetre long silicon microneedles at a skin depth where no blood capillaries exist.

An example of such a microneedle is disclosed in WO 2017/095321. In this publication is disclosed a microneedle having a capillary bore extending in the longitudinal direction and having an opening close to the distal end. The proximal end is connected to a substrate on which the microneedle is provided. In this example, the distal end is configured with a bevel.

Glucose sensors are known in the art. One known type of glucose sensor is the Clark biosensor. This sensor is based on a thin layer of glucose oxidase (GOx) on an oxygen electrode. The readout is the amount of oxygen consumed by GOx during enzymatic reaction with the substrate glucose. A more detailed description of biosensors, such as the Clark type, can be found in Anthony P. F. Turner: Biosensors: sense and sensibility, *Chem. Soc. Rev.*, Volume 42, Number 8, 21 Apr. 2013, pages 3175-3648. The described biosensors may be used in the present context.

SUMMARY OF THE INVENTION

An object of the present disclosure is to provide an improved apparatus for sampling a bodily fluid, as well as an improved method.

These objects are achieved by the device, the apparatus and the method according to the appended claims.

The invention is inter alia based on the realization that by providing a device that can provide a suction effect in a simple manner, an apparatus for sampling a bodily fluid can be improved.

According to a first aspect of the invention, there is provided a suction applying device for applying suction to a sampling unit for sampling bodily fluid, wherein the suction applying device comprises
  a syringe body with a hollow interior and a piston movable inside the hollow interior of the syringe body, wherein the syringe body has a rear end through which a piston rod connected to the piston extends outside of the syringe body and by means of which the piston can be moved, and a front end opposite the rear end,
  a connection arrangement configured for connection of a sampling unit, wherein the connection arrangement is located at the front end of the syringe body,
  a first conduit having a rear opening connecting the first conduit to a rear portion of the hollow interior of the syringe body, in which rear portion a sub-pressure is created when the piston is moved forward inside the hollow interior, and a front opening by means of which the first conduit is connectable to a sampling unit, and
  a second conduit, which second conduit connects a front portion of the hollow interior of the syringe body, with the exterior of the syringe body, and which front portion is located between the piston and the front end of the syringe body.

This suction applying device has the advantage that a suction effect can be achieved when the piston is moved downwards in the syringe body. Thus, when a sampling unit is connected at the front end of the syringe body, the sampling unit can be subjected to the suction force. The hollow interior of the syringe body is divided into two portions by the movable piston. A rear portion is the portion of the hollow interior that is located between the rear end of the syringe body and the piston, and a front portion of the hollow interior that is located between the piston and the front end of the syringe body. The piston should initially be positioned in a rear position in the hollow interior. When the piston is pushed forward inside the hollow interior, an increasing sub-pressure will be created in the rear portion of the hollow interior, i.e. the hollow interior between the piston and the rear end of the syringe body, and also in the first conduit having a rear opening connecting the first conduit to the rear portion of the hollow interior of the syringe body. Thus there will be a sub-pressure at the front opening of the conduit, as long as this opening is not in communication with the surroundings. Thus, if a sampling unit is connected to the front opening of the first conduit, the sampling unit will be affected by the sub-pressure and a suction effect is applied to the sampling unit. The first conduit thus functions as a suction conduit. The forward movement of the piston inside the hollow interior is facilitated by the existence of the second conduit by means of which air inside the front portion of the hollow interior, i.e. air in the hollow interior between the piston and the front end of the syringe body, may be evacuated to the exterior. The second conduit thus can be described as functioning as an evacuation conduit or pressure equalizing conduit.

The second conduit connects a front portion of the hollow interior of the syringe body with the exterior of the syringe body. The front portion is located between the piston and the front end of the syringe body. This will ensure that the air pressure (or other gas if applicable) inside the hollow interior, at the front end will be the same air pressure as in the surroundings of the device. If the piston should be placed at the front end of syringe body, air from outside will be sucked into the hollow interior, via the second conduit, as soon as the piston is moved backwards in the syringe body, i.e. towards the rear end of the syringe body. Thus the air pressure inside the hollow interior, in front of the piston will always be the same as the air pressure externally of the syringe body.

Consequently, a suction effect can be applied to a sampling unit connected to the suction applying device, by moving the piston forward in the syringe body. By obtaining suction effect during a forward motion of the piston, it will be easier to keep the sampling device in permanent and reliable contact with the skin of the person from which a sample is to be taken, since the forward motion will also press the sampling device against the skin. This is contrary to the conventional syringe in which the piston is moved backward in the syringe body when a suction force is to be obtained, by pulling at the piston rod. With a conventional syringe device, the user has to pull at the piston rod and at the same time push on the syringe body in order not to lose contact between the sampling device and the skin. With the suction applying device of the present disclosure, the user only has to push in one direction, namely forward, in order to obtain a suction effect when obtaining a sample. Thus with the new suction applying device, the process of taking a sample of bodily fluid is made more reliable, simple and safe. E.g. there will be a lesser risk of the needles being pulled out involuntarily during the sampling procedure. Another advantage is that the sub-pressure is built up continuously and therefore the suction effect will not occur suddenly, but instead there will be a continuous suction effect which will be more merciful for the patient and less unpleasant. There is also an hygienic advantage when the microneedles can be applied to the skin of the patient by means of the suction applying device, instead of e.g. by a finger.

The connection arrangement configured for connection of a sampling unit may comprise a compartment configured for housing a sampling unit, and said front opening of the first conduit leading into the compartment.

The connection arrangement of the suction applying device may comprise a holder device for fixating a sampling unit to the suction applying device. When there is a compartment, the holder device is configured to fixate the sampling unit in the compartment. Such a holder device can be configured in many different ways, depending on the geometry and type of the sampling device that is to be used.

Generally, when a sampling device is fixated to the suction applying device, it should be fixated in a sealing manner. If necessary, special sealing means can be provided. If the sampling device is fixated in a compartment configured for housing the sampling unit, the compartment should be sealed, e.g. by means of the sampling device. If necessary, there may be provided sealing means either in the compartment or on the sampling device.

The connection arrangement may in particular be suitable for and configured for connection of a sampling unit comprising a microneedle device, e.g. in a chip form as disclosed in WO 2017/095321.

The connection arrangement may comprise at least one electrical contact, by means of which electric connection of a sampling unit to the suction applying device can be provided. This makes it possible to connect a sampling unit to e.g. electric devices provided in or on the suction applying device.

The suction applying device may comprise a detection unit configured for digitalization of a measurement derived from an extracted sample of bodily fluid, wherein said measurement is related to the presence of a component to be detected in the bodily fluid. This will have the advantage that sampling and a measurement result from a sampling unit can be processed in one and the same device, namely the suction applying device. There is no need for any auxiliary device to process an obtained sample and obtain a measurement result. The measurement may be a measurement of an entity related to the presence of a component to be detected in the bodily fluid.

The suction applying device may comprise a display device configured for displaying a result obtained from the detection unit. This also provides the advantage of the possibility to have only one device and not having to move the sample to a separate unit for processing.

According to a second aspect there is provided an apparatus for sampling bodily fluid, comprising
  a suction applying device according to anyone of the claims defining such a device,
  a sampling unit comprising a microneedle device, which microneedle device comprises a plurality of hollow microneedles configured for extraction of a sample of bodily fluid, and said sampling unit further comprising a sample recipient device configured for receiving bodily fluid extracted by the microneedle device, and said sampling unit being connected to the suction applying device, whereby a suction force can be applied to the microneedles of the microneedle device.

In addition to advantages obtained by the suction applying device, as described above, this apparatus provides the advantage that the penetration of the skin by the microneedle device can be performed immediately before the suction of the sample of bodily fluid, and more or less in one movement, by pressing the syringe with the microneedles against the skin such that they penetrate the skin and then continue by pressing on the piston rod to move the piston forward and thus applying suction force to the sampling unit and the microneedles.

In more precise terms, the apparatus may comprise a fluid path provided in the sampling unit between the microneedle device and the sample recipient device, and the fluid path continues from the sample recipient device to the front opening of the first conduit, whereby the fluid path forms a suction path such that a suction force can be applied from the front opening of the first conduit to the microneedle device, when the piston is moved in a direction towards the front end of the syringe body.

Preferably, the sampling unit, or at least a part of it, is detachable from the suction applying device and replaceable. Generally, it is foreseen that the sampling unit can be a disposable unit, while the suction applying device is a base unit that is intended for multiple use.

In one example, the sample recipient device of the sampling unit may comprise a filter member configured for absorbing bodily fluid that is extracted by the microneedle device. This is a simple form of sampling unit. As an alternative, the filter member may be prepared with a reagent that changes a physical or chemical property of the filter member when in contact with a component to be detected in the bodily fluid. In the first alternative, the sampling unit with the filter member, after having received a sample of bodily fluid, will normally be removed from the apparatus and the sample will be processed in another device, usually some type of measuring device, e.g. a glucometer or liquid chromatography and mass spectrometry equipment (LC-MS), to detect the component to be detected. The sample could be treated with some reagent in that other device before a measurement would be performed. If instead the filter member is already prepared with a reagent, then that second device will not have to deal with any reagents, only the measurement.

According to another example, the sampling unit may comprises a sensor device configured for detecting the presence of a component to be detected in the bodily fluid, and wherein said sensor device comprises said sample recipient device. This has the advantage of requiring less handling of the sample, since the sample does not have to be moved to another unit for processing. Instead the sensor device would be able to perform certain measures and can present some kind of measurement result. In order to interpret this result into a language understandable by a user, the result may still have to be processed in another external unit. Or such facilities may be provided by and/or integrated in the suction applying device.

The sensor device may be configured to provide a measurement related to the presence of a component to be detected in the bodily fluid. This represents a common use, e.g. for detecting the level of glucose in the sample of bodily fluid. The measurement may be a measurement of an entity related to the presence of a component to be detected in the bodily fluid.

The sensor device may comprise at least one electrical contact element that is connectable to at least one electrical contact provided as part of the connection arrangement, and by means of which electric connection of the sampling unit to the suction applying device can be provided. This will make it possible to provide means for read out of the sample result on the suction applying apparatus. For example by means of a detection unit incorporated in the suction applying device and configured for digitalization of a measurement derived from an extracted sample of bodily fluid, and also by means of a display device incorporated on the suction applying device.

According to one example, the sensor device may comprise an electrochemical sensor, and wherein a reagent configured to react when in contact with a component to be detected in the bodily fluid is provided in the sample recipient device.

According to another example, the sensor device may comprise a RF sensor. For example an RF sensor device in combination with a microneedle device as described in WO 2015/187066.

The concerned bodily fluid may be blood and/or interstitial fluid. The apparatus may be used for measuring e.g. glucose, i.e. the component that it is desired to detect may be glucose. It may also be used for sampling any other fluid as the case may be.

The reagent in the filter or the cavity of the sensor device may e.g. be a protein, an enzyme e.g. oxidase reagent, or any other reagent suitable for converting the component in the bodily fluid that it is desired to detect into a detectable signal.

According to a third aspect there is provided a method for detecting a component in a bodily fluid, comprising
   providing an apparatus according to any one of the claims defining such an apparatus,
   applying the front end of the suction applying device with the microneedle device onto the stratum corneum of a person, and applying a pressure force onto the apparatus such that the microneedles penetrate the stratum corneum into epidermis,
   pushing the piston towards the front end of the syringe body and creating a suction force through the first conduit and the sampling unit whereby a suction force is created in the microneedles, whereby bodily fluid is extracted through the microneedles and further directed to the sample recipient device of the sampling unit,
   performing a measurement of the extracted sample of bodily fluid in a sensor device, wherein the measurement is a measurement related to the presence of a component to be detected in the bodily fluid, and
   detecting the component based on the performed measurement.

The method may also comprise optional additional steps of performing digitalization of the measurement and presenting the result derived from the detection of the component on a display unit.

Further features and advantages of the invention will also become apparent from the following detailed description of embodiments.

BRIEF DESCRIPTION OF THE DRAWINGS

The invention will now be described in more detail, with reference being made to the enclosed schematic drawings illustrating different aspects and embodiments of the invention, given as examples only, and in which.

Elements that are the same or represent corresponding or equivalent elements have been given the same reference numbers in the different figures.

DETAILED DESCRIPTION

Figure 1:
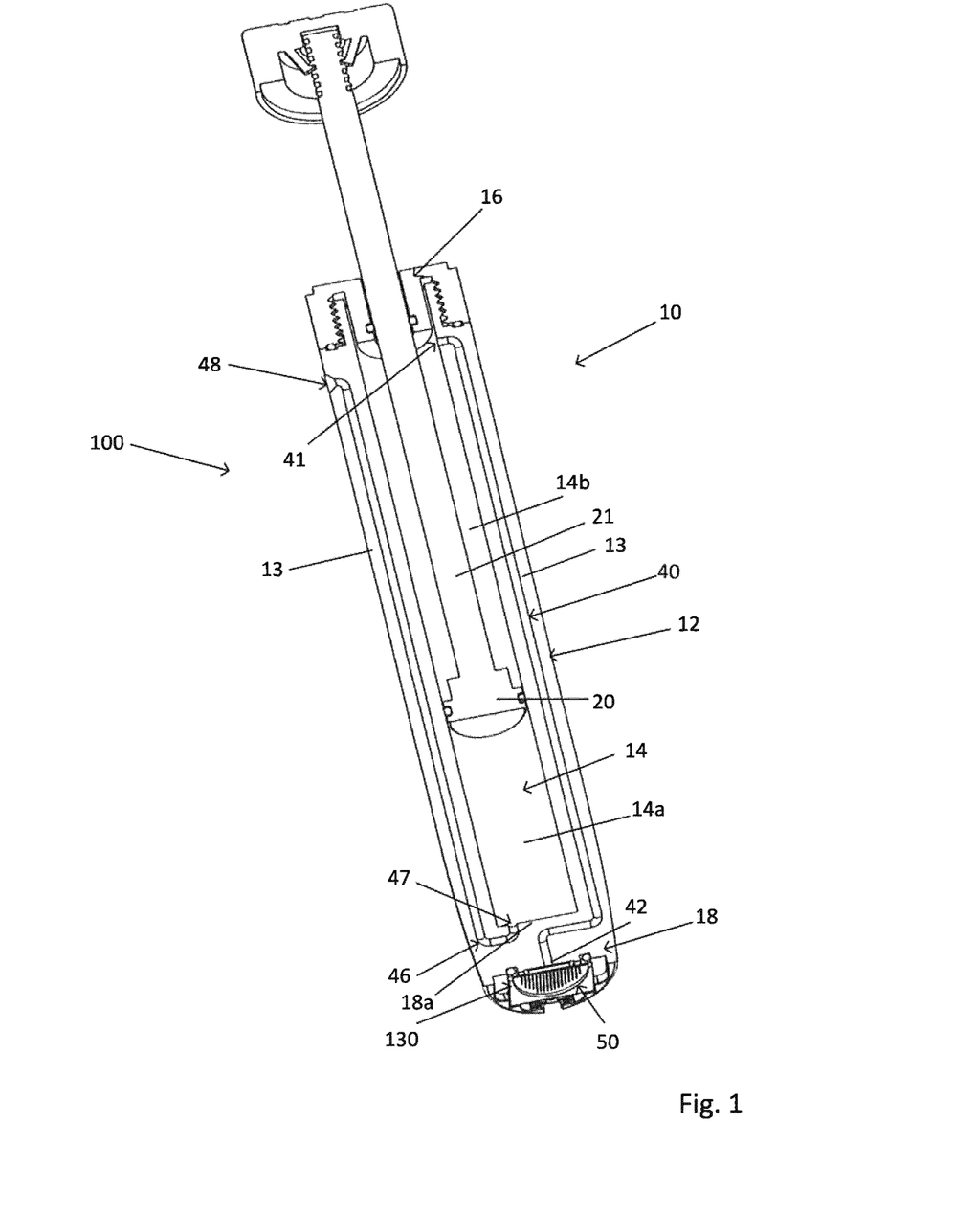
FIG. 1 shows a partly perspective, cross section view of a suction applying device.

In FIG. 1 is shown a cross section of a suction applying device 10 for applying suction to a sampling unit 50 for sampling bodily fluid. The suction applying device 10 comprises a syringe body 12 with a hollow interior 14 and a piston 20 movable inside the hollow interior of the syringe body. The syringe body 12 has a rear end 16 through which a piston rod 21 connected to the piston 20 extends outside of the syringe body 12 and by means of which the piston can be moved. The syringe body also has a front end 18 opposite the rear end 16.

Figure 2:
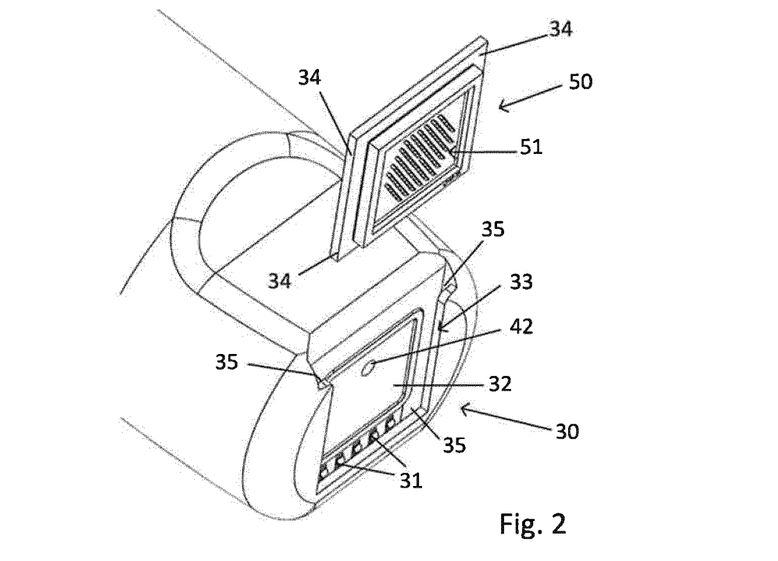
FIG. 2 shows an enlarged partial view of an apparatus for sampling bodily fluid, according to a first example.

The suction applying device comprises a connection arrangement 30, as shown in FIG. 2, configured for connection of a sampling unit 50, which connection arrangement is located at the front end 18 of the syringe body 12.

The suction applying device 10, as shown in FIG. 1, further comprises a first conduit 40 having a rear opening 41 connecting the first conduit to the rear portion 14b of the hollow interior 14 of the syringe body 12, and a front opening 42, by means of which the first conduit 40 is connectable to the sampling unit 50. In the rear portion, a sub-pressure is created when the piston is moved forward inside the hollow interior. The suction applying device 10 also comprises a second conduit 46 that connects the front portion 14a of the hollow interior 14 of the syringe body 12, with the exterior of the syringe body. The front portion 14a is located between the piston 20 and the front end 18 of the syringe body. In other words, the hollow interior 14 of the syringe body is divided into two portions 14a, 14b by the movable piston 20. A rear portion 14b is the portion of the hollow interior that is located between the rear end of the syringe body and the piston, and a front portion 14a of the hollow interior that is located between the piston and the front end of the syringe body.

By suction applying is meant that the device is capable of creating a sub-pressure in relation to the surrounding atmospheric pressure, i.e. an air pressure, or gas pressure, that is below the pressure in the surrounding atmosphere. In particular it is capable of creating sub-pressure and a suction effect in a sampling unit when such a sampling unit is connected to the suction applying device.

The suction applying device 10 functions as follows. When the piston 20 is retracted in the hollow interior 14 as far as possible, it will stop at the rear end 16 of the syringe body 12. In this retracted position, the piston 20 will block the rear opening 41 of the first conduit 40. When the piston 20 is pushed forward inside the hollow interior 14, the rear opening 41 of the first conduit 40 will become free. As the piston continues to be moved forward, by pushing on the piston rod, an increasing sub-pressure will be created in the rear portion 14b of the hollow interior 14 and also in the first conduit 40. In the case when there is a sampling unit 50 connected to the suction applying device 10, the front opening 42 of the first conduit 40 will be connected to the sampling unit 50 and thereby the sampling unit will be affected by the sub-pressure and a suction effect is applied to the sampling unit. The first conduit 40 thus functions as a suction conduit. It should be mentioned that the forward movement of the piston 20 inside the hollow interior is facilitated by the existence of second conduit 46 by means of which air inside the front portion 14a of the hollow interior 14 may be evacuated to the exterior. The second conduit thus can be described as functioning as an evacuation conduit.

In a conventional way, the piston 20 will be configured to fit snugly into the hollow interior 14 such that air should not be allowed to pass between the piston and the syringe wall, from the rear portion 14b of the hollow interior to the front portion 14a, or vice versa. If necessary, the piston may be provided with some sort of external seal that will improve the sealing effect between the piston and the syringe wall.

Naturally, the piston does not have to be retracted all the way to the rear end 16 of the syringe body 12, and it does not have to block the rear opening 41 of the first conduit 40. A sub-pressure will be created in the rear portion 14b of the hollow interior 14 as soon as the piston 20 is moved forward, and a suction effect will be created in the first conduit 40, even if the piston starts the forward motion further down in the hollow interior. The suction effect will be created as soon as the rear opening is in communication with the portion of the hollow interior 14 that is between the piston 20 and the rear end 16 of the syringe 12 when the piston is moved forward, and this portion will be the rear portion 14b.

The connection arrangement 30 may comprise a compartment 32 configured for housing a sampling unit 50, and said front opening 42 of the first conduit 40 leading into the compartment. This is schematically illustrated in FIGS. 2-4a, illustrating different examples of a connection arrangement 30, 130, 230 with a compartment 32, 132, 232.

The connection arrangement may comprise a holder device 33, 133, 233 for fixating a sampling unit 50 to the suction applying device. When there is a compartment, the holder device is preferably configured to fixate the sampling unit in the compartment.

Figure 3:
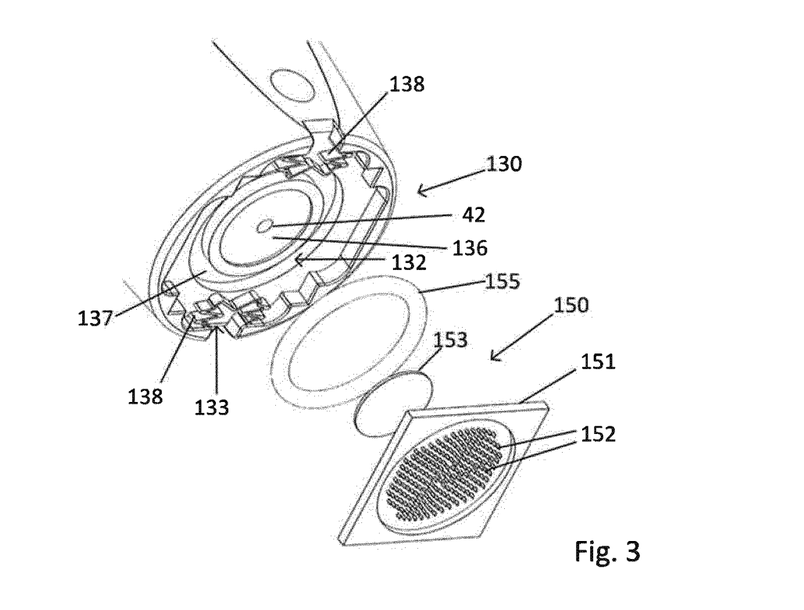
FIG. 3 shows an enlarged partial view of an apparatus for sampling bodily fluid, according to a second example.

The connection arrangement 30 may comprise at least one electrical contact 31, by means of which electric connection of a sampling unit 50 to the suction applying device 10 may be provided. Such electrical contacts may e.g. be spring-loaded metal plates as schematically illustrated in FIG. 3.

In the illustrated example of FIG. 1, the details of the connection arrangement have been illustrated as pertaining to a sampling unit 50 as shown in FIG. 2. However, different variants of the connection arrangement and the sampling unit are foreseen, as will be described below.

The above described details of the connection arrangement, e.g. electric contacts, compartment, holder device, can be used in combination or each one separately without the others. Different variants of such a holder device will be described later.

Figure 7:
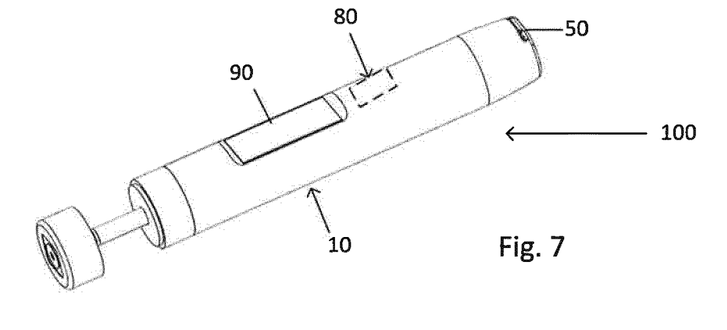
FIG. 7 illustrates a variant of a suction applying device.

The suction applying device may comprise a detection unit 80 configured for digitalization of a measurement derived from an extracted sample of bodily fluid. The sample is obtained by the sampling unit. The measurement is a measurement related to the presence of a component to be detected in the bodily fluid. The suction applying device may also comprise a display device 90 configured for displaying a result obtained from the detection unit 80. This is illustrated in FIG. 7. The detection unit as well as the display unit may be implemented in many different ways, by using known technology.

In all of the FIGS. 1-4b, the suction applying device 10 is illustrated together with a sampling unit 50, which combination forms an apparatus 100 for sampling bodily fluid. However, it is stressed that the suction applying device 10 can be used together with many different types of sampling units, and it is not limited to use with the illustrated sampling units, or the examples of sampling units that are described in this disclosure.

The suction applying apparatus as such may also comprise details according to the following examples, which details may be comprised separately or in combination.

The first conduit 40 may be configured as a conduit made in the longitudinal wall 13 of the syringe body 12. Usually the syringe body would have a cylindrical shape with a longitudinal wall 13 extending between the rear end 16 and the front end 18 of the syringe body. Also the second conduit 46 may be configured as a conduit made in the wall of the syringe body 12. The second conduit would then have a first opening 47 into the hollow interior 14 located at the front end 18 of the syringe body. Preferably this first opening would be located in the front end wall 18a of the syringe body in order to be able to provide evacuation of air from the hollow interior 14 to the surroundings. The second conduit 46 would also then have a second opening 48 into the surrounding of the suction applying device. This second opening may be located anywhere on the exterior of the syringe, for example at the rear end 16 of the syringe body as shown in FIG. 1. In that case, the conduit would extend in the front end wall 18*a* of the syringe body and further in the longitudinal wall 13 of the syringe body.

In FIGS. 2-4*b* are illustrated examples of compartments for receiving a sampling unit and examples of holder devices. Also different examples of sampling units are schematically illustrated.

In FIG. 2 is shown a front end 18 of a syringe body 12. In the front end wall 18*a*, facing outwards, is provided a connection arrangement 30 having a compartment 32 configured for receiving a sampling unit 50. The front opening 42 of the first conduit 40 is also shown in FIG. 2 and it is shown as opening into the compartment. The interior of the compartment 32 will thus be in communication with the rear portion 14*b* of hollow interior 14, at the rear end 16 of the syringe body, via the first conduit 40. In this example, the sampling unit 50 is configured as a rectangular chip. The details of the sampling unit will be described below. The sampling unit has a protruding side edge 34, at least along three sides thereof. The compartment has a shape that essentially corresponds to the shape of the sampling unit 50 and it has corresponding grooves 35 along three of its sides, while one side is open and adapted for insertion of the sampling unit 50. When the sampling device is being inserted, its protruding side edges 34 will enter into the grooves 35 and the sampling unit will thus be fixated by a holder device 33 comprising the cooperating side edges 34 and the grooves 35. In FIG. 2 is also shown electric contacts 31 located at the far side of the compartment, which are designed to enter into electrical contact with corresponding electrical contact elements that may be provided on the sampling unit 50. Naturally, such electric contacts may be located elsewhere in the compartment or compartment walls.

In FIG. 3 is shown another variant of a connection arrangement 130. In this example, the sampling unit 150 comprises a chip comprising a microneedle device 151, a filter member 153 functioning as a sample recipient device, and a sealing member 155, as shown in the schematic exploded view. The compartment 132 comprises a recess 136 configured to receive the filter member. The recess is located such that the front opening 42 of the first conduit faces towards the filter member, when the filter member is placed in the recess. The compartment further includes a seat 137 for the sealing member 155, which seat is located externally of the filter recess. The connection arrangement also comprises a spring arrangement, comprising two spring members 138, by means of which the microneedle device 151 of the sampling unit 150 is fixated in the compartment 132. The spring members 138 thus function as holder devices 133. An additional snap function may also be provided in connection with the spring members or otherwise. When the sampling unit is fixated in the compartment 132, the filter member 153 will be in contact with the conduit opening 42, and the sealing member 155 will function as a seal between the filter member 153 and the microneedle device 151, such that a suction force applied through the conduit opening 42 will result in a suction force applied through the microneedles 152 of the microneedle device 151 and into the skin layer that is penetrated by the needles.

Figure 4A:
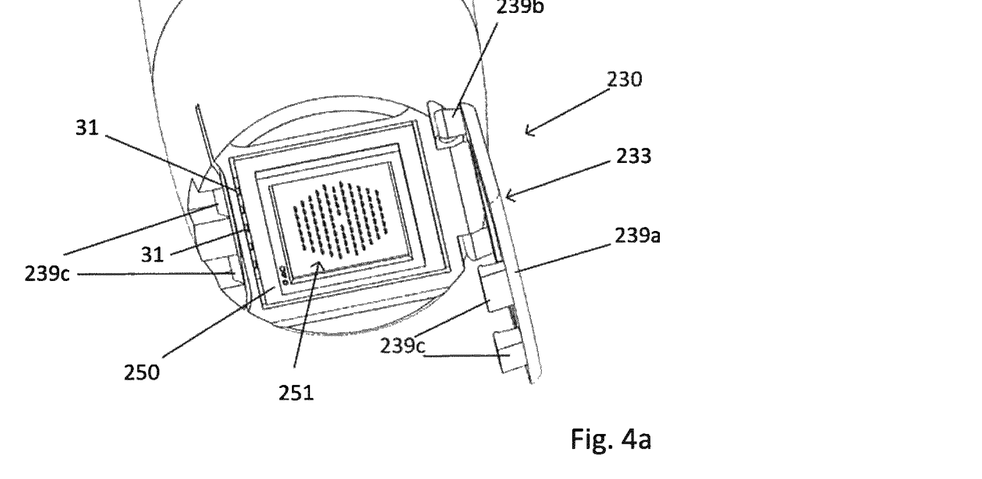
FIG. 4a and FIG. 4b show an enlarged partial view of an apparatus for sampling bodily fluid, according to a third example.
Figure 4B:
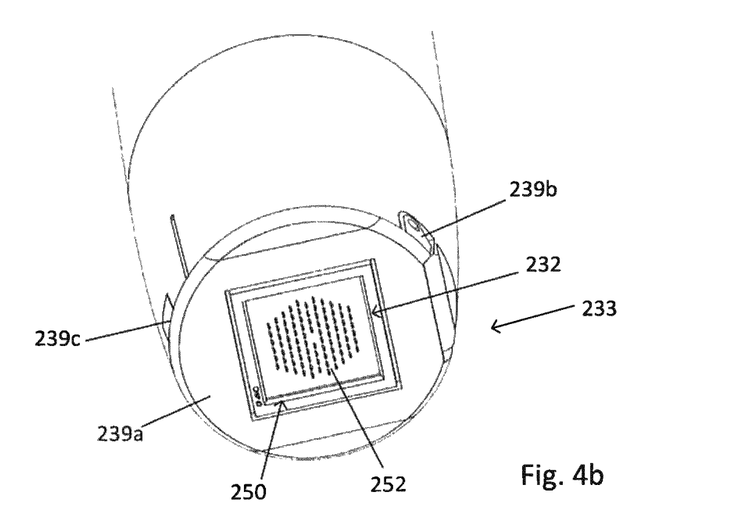

In FIGS. 4*a* and 4*b* is schematically illustrated another variant of a connection arrangement 230. The sampling unit 250 is schematically illustrated as being of the type illustrated in FIG. 2, but it may alternatively be of the type illustrated in FIG. 3 or another type, with the corresponding configuration of the compartment for receiving the sampling unit and for applying suction. The sampling unit 250 is placed in the compartment 232 and it is fixated by a holder device 233. The holder device 233 comprises a frame structure 239*a* that is attached to the front end 18 of the syringe body 12 by means of a hinge device 239*b*. When applied over the sampling unit 250, as shown in FIG. 4*b*, the frame structure 239*a* will surround the sampling unit while leaving the microneedles of the microneedle device 251 free, such that they can enter into contact with the skin of a person when extracting a sample. The frame structure 239*a* may be locked to the front end 18 of the syringe body 12 by means of a snap lock 239*c*, after having been placed in the appropriate fixating position over the sampling unit 250. The geometric shape of the frame structure may vary, both with regard to the outer shape and the shape of the internal opening. Possible shapes are essentially rectangular, circular, or combinations thereof.

An apparatus for sampling a bodily fluid is obtained when a suction applying device 10 as described above is combined with a sampling unit, e.g. a sampling unit 50, 150, 250. Generally, the sampling unit comprises a microneedle device 51, 151, 251, which microneedle device comprises a plurality of hollow microneedles 52, 152, 252 configured for extraction of a sample of bodily fluid, and said sampling unit further comprises a sample recipient device 53, configured for receiving bodily fluid extracted by the microneedle device 51, 151, 251, and said sampling unit 50, 150, 250 being connected to the suction applying device 10, whereby a suction force can be applied to the microneedles of the microneedle device. When suction is applied to the microneedles 52, 152, 252, they can then extract bodily fluid when the microneedles have penetrated the skin of a person, and the bodily fluid is then directed to and received by the sample recipient device 53.

Thus, when the sampling unit 50, 150, 250 is connected to the suction applying device 10, a fluid path is provided in the sampling unit between the microneedle device 51, 151, 251, and the sample recipient device 53, and the fluid path continues from the sample recipient device to the front opening 42 of the first conduit 40, whereby the fluid path forms a suction path such that a suction force can be applied from the front opening 42 of the first conduit 40 to the microneedle device 51, 151, 251, when the piston 20 is moved in a direction towards the front end 18 of the syringe body 12.

Preferably, the sampling unit, or at least a part of it, is detachable from the suction applying device and replaceable. Generally, it is foreseen that the sampling unit can be a disposable unit, while the suction applying device is a base unit that is intended for multiple use.

Some examples of a sampling unit have already been very briefly described above in connection with the description of the connection arrangement of the suction applying device.

One example of a sampling unit 150 is shown in FIG. 3. The sampling unit comprises a microneedle device 151, which microneedle device comprises a plurality of hollow microneedles 152 configured for extraction of a sample of bodily fluid. The sampling unit further comprises a sample recipient device configured for receiving bodily fluid extracted by the microneedle device and in this example the sample recipient device comprises the filter member 153. The sampling unit may also comprise the sealing member 155, or alternatively, the sealing member may be a separate part located in the compartment 132, and not forming part of the sampling unit.

When the sampling unit 150 is attached to the suction applying device 10, a suction force can be generated at the front opening 42 of the first conduit 40 by moving the piston 20 forward in the hollow interior 14 of the syringe body 12. The suction force will act through the filter member 153 applied over the front opening 42 and through the hollow microneedles 152, whereby a sample of bodily fluid can be extracted through the microneedles when they have penetrated the skin, the stratum corneum, and into epidermis of the person from which a sample is required. Bodily fluid will then be directed from the microneedles and into the filter member 153 that will act as a sample recipient device. The sampling unit can then be removed and the filter member with the collected sample of bodily fluid can be analysed in a separate apparatus, usually comprising some type of sensor device.

In one variant, the filter member may be prepared with a reagent that changes a physical or chemical property of the filter member when in contact with a component to be detected in the bodily fluid. The filter member will then offer a pre-stage for the analysis to be made. Indeed it is also possible that an analysis is not required but a simple measurement may be sufficient. If the property is a physical property, it may even be possible to have a visible indication related to the component to be detected just from looking at the filter member.

According to another example, the apparatus comprises a sampling unit comprising a sensor device configured for detecting the presence of a component to be detected in the bodily fluid, and wherein said sensor device comprises said sample recipient device. An example of a sampling unit 50; 250 with a sensor device 56 is schematically illustrated in FIG. 2 and FIGS. 4a-4b.

In one example, the sensor device may be configured to provide a measurement of an entity related to the presence of a component to be detected in the bodily fluid.

The sensor device may comprise at least one electrical contact element that is connectable to at least one electrical contact provided as part of the connection arrangement, and by means of which electric connection of the sampling unit to the suction applying device can be provided.

Figure 5:
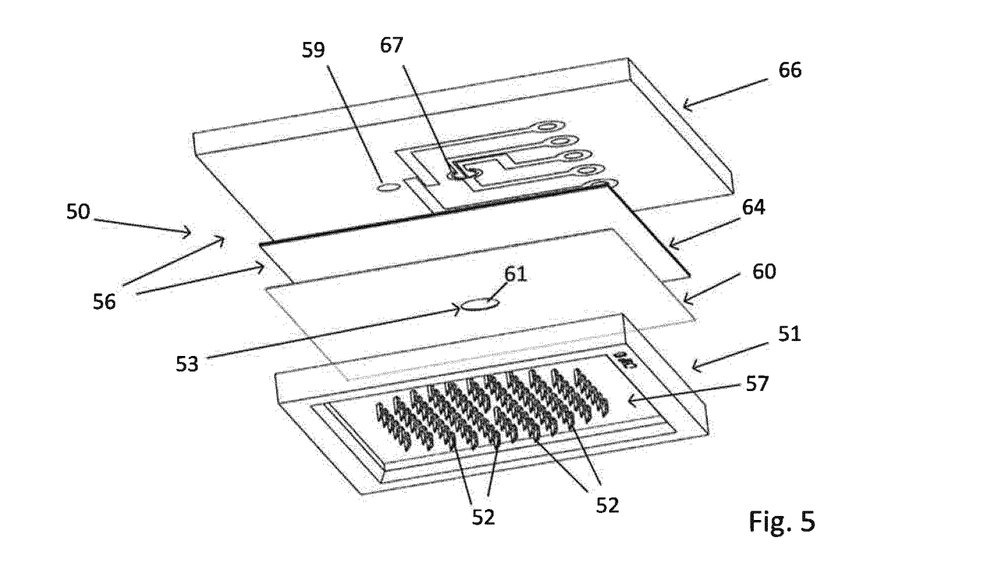
FIG. 5 shows a detail of an apparatus for sampling bodily fluid.
Figure 6:
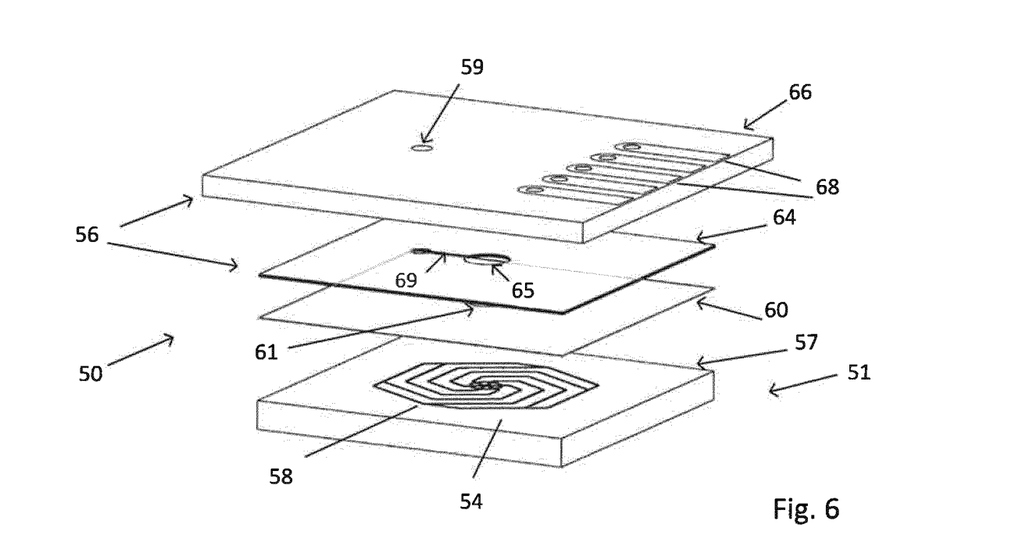
FIG. 6 shows another view of the detail in FIG. 5.

An example of a sensor device 56 is illustrated in FIGS. 5 and 6. In this example, the sensor device is an electrochemical sensor device. The sensor device 56 comprises a sample recipient device 53 comprising a cavity 65. The sensor device 56 is part of a sampling unit 50 or 250, as described above.

In FIGS. 5 and 6, a sampling unit 50 comprises a microneedle device 51 that comprises a plurality of microneedles 52 located on a first substrate 57. In FIG. 5 the sampling unit 50 is illustrated in an exploded view from below, showing a downside or front side of the components of the sampling unit, and showing the microneedles 52 that are intended to be inserted into a person's skin. In FIG. 6 the sampling unit 50 is illustrated in an exploded view from above, showing the upper or back side of the components of the sampling unit.

Each microneedle 52 comprises a capillary bore that defines a first fluid path for an extracted bodily fluid sample. The first fluid path is in fluid communication with a fluid channel 58 of the first substrate 57. The microneedle device 51 further comprises a second substrate 60 that comprises a first fluid port 61 in fluid communication with the fluid channel 58 of the first substrate 57. This substrate functions as a capillary closing layer. The sampling unit 50 further comprises a sensor device 56, which in this example is an electrochemical sensor device. The sensor device may for example be of the Clark type of electrochemical sensor.

In the illustrated example, the electrochemical sensor device comprises two layers, a cavity forming layer 64 and a layer comprising an electrochemical transducer element 66. The cavity forming layer comprises a cavity 65 functioning as a sample recipient device. The cavity comprises a reagent that is chosen such that it will generate a chemical reaction when coming into contact with a component of the bodily fluid that it is desired to detect. This reaction will then influence an active area 67 the transducer element 66 and the chemical changes will be transformed into electrical signals. These signals will reflect a measurement of an entity related to the presence of the component to be detected. The cavity 65 is in fluid communication with the first fluid port 61 such that a fluid path for an extracted bodily fluid is created from each microneedle 52 to the cavity. The cavity layer 64 further comprises a connection path 69 that connects the cavity 65 with a through hole 59 in the transducer 66, which through hole is connectable with the front opening 42 of the first conduit 40 of the suction applying device. Thereby, the suction force generated at the front opening 42 can be transferred to the microneedles of the microneedle device.

As shown in the example, the first fluid path extends from a first lower opening in the microneedle 52 into the capillary bore, which lower opening is in contact with the bodily fluid, to a second upper opening in the capillary bore which opening is located on the opposing upper side 54 of the first substrate 57. The openings of the capillary bores of the microneedles in the upper side 54 are all connected to the fluid channel 58. E.g. in the pattern illustrated in FIG. 6.

The microneedles 52 may for example be integrated into the first substrate 57.

In FIG. 2 is illustrated a sampling unit as it looks after the different components of the sampling unit 50 have been assembled.

When the different components of the sampling unit 50 are assembled and the sampling unit is connected to the front end 18 of the syringe body 12 of the suction applying device 10 by means of the connection arrangement 30, as shown in FIGS. 1 and 2, the through hole 59 of the sensor device 56 will be located such that communication is achieved with the front opening 42 of the first conduit 40. Thus a suction force can be generated at the front opening 42 of the first conduit 40 by moving the piston 20 forward in the hollow interior 14 of the syringe body 12. The suction force will act through the front opening 42 and via the sensor device 56 and through the hollow microneedles 52, whereby a sample of bodily fluid can be extracted through the microneedles when they have penetrated the skin, the stratum corneum, and into epidermis of the person from which a sample is required. Bodily fluid will then be directed from the microneedles and into the cavity 65 that will act as a sample recipient device.

The sensor device 56 preferably comprises at least one electrical contact element 68 that is connectable to at least one electrical contact 31 provided as part of the connection arrangement 30 of the suction applying device 10. Electric connection of the sampling unit to the suction applying device can therefore be provided. An electric signal from the sensor device 56 can then be transmitted to the detection unit 80 forming part of the suction applying device. As mentioned, the electric signal from the transducer element 66 of the sensor device will reflect a measurement of an entity related to the presence of the component to be detected. The detection unit can then perform digitalization of said measurement derived from an extracted sample of bodily fluid. A display device 90 located on the suction applying device 10 can then be configured to display a result obtained from the detection unit, as shown in FIG. 7.

As an alternative to an electrochemical sensor device, it is possible to use a RF sensor device in combination with a microneedle device. For example an RF sensor device as described in WO 2015/187066.

The concerned bodily fluid may be blood and/or interstitial fluid. The apparatus may be used for measuring e.g. glucose, i.e. the component that it is desired to detect may be glucose.

The reagent in the filter or the cavity of the sensor device may e.g. be a protein, an enzyme, e.g. an oxidase reagent, or any other reagent suitable for the component in the bodily fluid that it is desired to detect.

Figure 8:
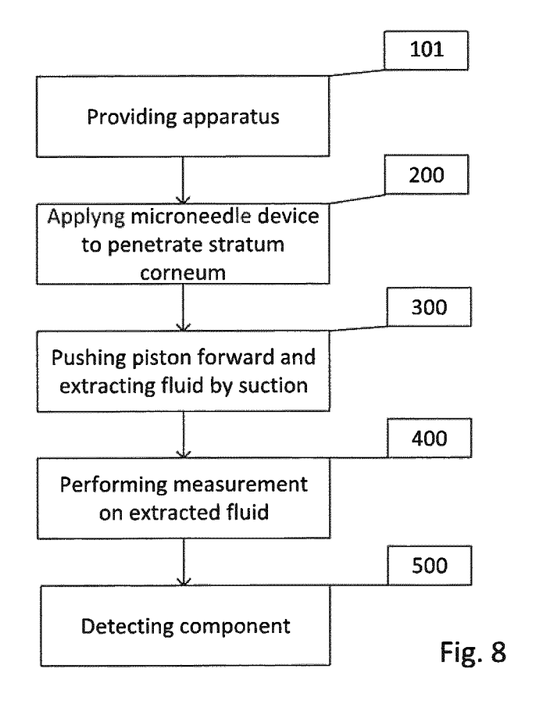
FIG. 8 is a diagram illustrating an example of a method.

A method for detecting a component in a bodily fluid is also disclosed and illustrated in FIG. 8. The method comprises the steps of:
- providing an apparatus in accordance with what has been described above (101),
- applying the front end of the suction applying device with the microneedle device onto the stratum corneum of a person, and applying a pressure force onto the apparatus such that the microneedles penetrate the stratum corneum into epidermis (200),
- pushing the piston towards the front end of the syringe body and creating a suction force through the first conduit and the sampling unit whereby a suction force is created in the microneedles, whereby bodily fluid is extracted through the microneedles and further directed to the sample recipient device of the sampling unit (300),
- performing a measurement of the extracted sample of bodily fluid in a sensor device, wherein the measurement is related to the presence of a component to be detected in the bodily fluid (400), and
- detecting the component based on the performed measurement (500).

The method may also comprise optional additional steps of performing digitalization of the measurement and presenting the result derived from the detection of the component on a display unit.

It should be mentioned that the sensor device mentioned in the method is not necessarily a sensor device forming part of the suction applying device, but it may alternatively be a sensor device provided as a separate unit.

It should also be mentioned that the variants of the sampling unit as such that has been described above, may form part of the apparatus or can be used separately or in another type of apparatus.

The invention shall not be considered limited to the illustrated embodiments, but can be modified and altered in many ways, as realised by a person skilled in the art, without departing from the scope defined in the appended claims.

The invention claimed is:

1. A suction applying device for applying suction to a sampling unit for sampling bodily fluid, wherein the suction applying device comprises:
- a syringe body with a hollow interior, a longitudinal wall surrounding the hollow interior, and a piston movable inside the hollow interior of the syringe body, wherein the syringe body has a rear end through which a piston rod connected to the piston extends outside of the syringe body and by means of which the piston can be moved, and a front end opposite the rear end,
- a connection arrangement configured for connection of a sampling unit, wherein the connection arrangement is located at the front end of the syringe body,
- a first conduit comprising a longitudinal tube having a front opening connected to the sampling unit by the connection arrangement and having a rear opening connecting the first conduit to a rear portion of the hollow interior of the syringe body, the first conduit extending longitudinally, from the front opening to the rear opening, through the longitudinal wall of the syringe body, wherein a sub-pressure is created in the rear portion of the hollow interior of the syringe body when the piston is moved forward inside the hollow interior, and
- a second conduit, which second conduit connects a front portion of the hollow interior of the syringe body with the exterior of the syringe body, and which front portion is located between the piston and the front end of the syringe body, wherein the second conduit comprises a longitudinal tube having a first opening into the front portion of the hollow interior of the syringe body, and a second opening through the syringe body to the exterior, wherein the second conduit extends through the longitudinal wall of the syringe body from the first opening to the second opening.

2. The suction applying device according to claim 1, wherein the connection arrangement configured for connection of a sampling unit comprises a compartment configured for housing a sampling unit, and said front opening of the first conduit leading into the compartment.

3. The suction applying device according to claim 1, wherein the connection arrangement comprises a holder device for fixating a sampling unit to the suction applying device.

4. The suction applying device according to claim 1, wherein the connection arrangement comprises at least one electrical contact, by means of which electric connection of a sampling unit to the suction applying device can be provided.

5. The suction applying device according to claim 1, further comprising a detection unit configured for digitalization of a measurement derived from an extracted sample of bodily fluid, wherein said measurement is related to a component to be detected in the bodily fluid.

6. The suction applying device according to claim 5, further comprising a display device configured for displaying a result obtained from the detection unit.

7. An apparatus for sampling bodily fluid, comprising the suction applying device and the sampling unit according to claim 1, wherein the sampling unit comprises a microneedle device, which microneedle device comprises a plurality of hollow microneedles configured for extraction of a sample of bodily fluid, and said sampling unit further comprising a sample recipient device configured for receiving bodily fluid extracted by the microneedle device, and said sampling unit is connected to the suction applying device, whereby a suction force can be applied to the plurality of hollow microneedles of the microneedle device.

8. The apparatus according to claim 7, wherein a fluid path is provided in the sampling unit between the microneedle device and the sample recipient device, and the fluid path continues from the sample recipient device to the front opening of the first conduit, whereby the fluid path forms a suction path such that a suction force can be applied from the front opening of the first conduit to the microneedle device, when the piston is moved in a direction towards the front end of the syringe body.

9. The apparatus according to claim 7, wherein the sample recipient device comprises a filter member configured for absorbing bodily fluid that is extracted by the microneedle device.

10. The apparatus according to claim 7, wherein the sampling unit comprises a sensor device configured for detecting the presence of a component to be detected in the bodily fluid, and wherein said sensor device comprises said sample recipient device.

11. The apparatus according to claim 10, wherein the sensor device is configured to provide a measurement related to the presence of a component to be detected in the bodily fluid.

12. The apparatus according to claim 10, wherein the sensor device comprises at least one electrical contact element that is connectable to at least one electrical contact provided as part of the connection arrangement, and by means of which electric connection of the sampling unit to the suction applying device can be provided.

13. The apparatus according to claim 10, wherein the sensor device comprises an electrochemical sensor, and wherein a reagent configured to react when in contact with a component to be detected in the bodily fluid is provided in the sample recipient device.

14. The apparatus according to claim 10, wherein the sensor device comprises a RF sensor.

15. A method for detecting a component in a bodily fluid, comprising
providing an apparatus according to claim 7,
applying the front end of the suction applying device with the microneedle device onto a stratum corneum of a person, and applying a pressure force onto the apparatus such that the microneedles penetrate the stratum corneum into epidermis,
pushing the piston towards the front end of the syringe body and creating a suction force through the first conduit and the sampling unit whereby a suction force is created in the microneedles, whereby bodily fluid is extracted through the microneedles and further directed to the sample recipient device of the sampling unit,
performing a measurement of the extracted sample of bodily fluid in a sensor device, wherein the measurement is related to the presence of a component to be detected in the bodily fluid, and
detecting the component based on the performed measurement.

* * * * *